United States Patent [19]

Fankhauser

[11] 4,336,197
[45] Jun. 22, 1982

[54] 6-ETHYL-2,10,10-TRIMETHYL-1-OXA-SPIRO[4.5]DECA-3,6-DIENE

[75] Inventor: Peter Fankhauser, Onex, Switzerland

[73] Assignee: Firmenich SA, Geneva, Switzerland

[21] Appl. No.: 230,406

[22] Filed: Jan. 30, 1981

[30] Foreign Application Priority Data

Feb. 8, 1980 [CH] Switzerland ................. 1013/80

[51] Int. Cl.³ ............................................. C07D 307/94
[52] U.S. Cl. ................................... 549/331; 426/536; 252/522 R
[58] Field of Search ................................ 260/346.11

[56] References Cited

U.S. PATENT DOCUMENTS 3,852,355 12/1974 Rautenstrauch et al. ... 260/346.11 X
4,011,245  3/1977 Naegeli ........................... 260/346.11
4,179,448 12/1979 Schulte-Elte et al. ......... 260/346.11

FOREIGN PATENT DOCUMENTS 2634077  2/1977 Fed. Rep. of Germany .
2749511 11/1977 Fed. Rep. of Germany .

Primary Examiner—Richard Raymond
Attorney, Agent, or Firm—Scully, Scott, Murphy and Presser

[57] ABSTRACT

New spiranic compound, viz. 6-ethyl-2,10,10-trimethyl-1-oxa-spiro[4.5]deca-3,6-diene, its preparation and use of same as perfume or flavor-modifying ingredient.

1 Claim, No Drawings

6-ETHYL-2,10,10-TRIMETHYL-1-OXA-SPIRO[4.5-]DECA-3,6-DIENE

SUMMARY OF THE INVENTION

The invention relates to a compound of formula

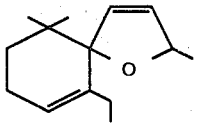

(I)

The invention also relates to a process for the preparation of the compound defined hereinabove, which comprises
(A) reacting 2-ethyl-6,6-dimethyl-cyclohexanone with but-1-yn-3-ol in the presence of a strong base or with an organo-metallic derivative of formula

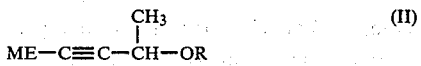

(II)

wherein symbol ME represents an alkali metal or a halogenomagnesium radical and R represents a trialkyl-silyl, tetrahydropyranyl, tert-butyl, 3-oxa-pent-2-yl, 3-oxa-but-2-yl or a Mg-halogen radical, hydrolyzing the thus obtained reaction product and finally treating the hydrolization product with an acidic reagent; or
(B) reacting 2-ethyl-6,6-dimethyl-cyclohex-2-en-1-one with an organometallic derivative of formula (II) as defined hereinabove, hydrolyzing the thus obtained reaction product, hydrogenating the hydrolization product and finally treating the obtained hydrogenation product with an acidic reagent.

The invention also relates to a process for improving, enhancing or modifying the flavour properties of artificial flavours, foodstuffs, beverages, pharmaceutical preparations or tobacco products, or the odour properties of perfumes, perfume bases, perfume compositions or perfumed products, which comprises adding thereto a small but effective amount of the compound of formula (I) defined hereinabove.

The invention more specifically relates to a process for imparting a black-currant type odour free from sulfury tonality to perfumes, perfume bases, perfume compositions or perfumed products, which comprises adding thereto a small but effective amount of the compound of formula (I) defined hereinabove.

The invention finally relates to a perfume or flavour-modifying composition, which comprises the compound of formula (I) defined hereinabove as organoleptically active ingredient.

BACKGROUND OF THE INVENTION

The fruity odour note typical of black-currant is particularly well appreciated in modern perfumery. Up to now however it could not be easily reproduced by making use of prior known ingredients, black-currant buds absolute e.g.: this expensive fragrant material of natural origin possesses in fact a rather complex odour wherein the typical fruity note is often associated with undesired tonalities. In the same context, one can cite synthetic compounds such as 2,6,9,10,10-pentamethyl-1-oxa-spiro[4.5]deca-3,6-diene and 2,6,9,10-tetramethyl-1-oxa-spiro[4.5]deca-3,6-diene, of formulae

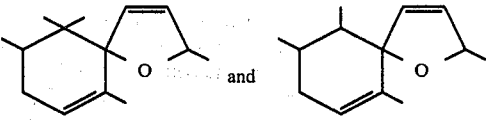

respectively, known in the art as possessing a fresh, green and natural odour reminiscent of that of mint leaves, clary sage and black-currant, as well as a fruity flavour more or less reminiscent of that of citrus fruits, grape-fruit more particularly [see DE-OS No. 2,634,077 and DE-OS No. 2,749,511, respectively].

Menthone-thiol-8 of formula

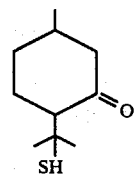

also develops a fruity odour of black-currant type, which odour is however associated with a sulfury tonality [see DE-PS No. 2,008,254]. Menthone-thiol-8 moreover is of limited interest in perfumery in view of its lack of stability in soaps, shampoos and detergents.

Contrary to the teaching of the art, the compound of formula (I), viz. 6-ethyl-2,10,10-trimethyl-1-oxa-spiro[4.5]deca-3,6-diene possesses a "clean" fruity note of black-currant type, namely free from any sulfury tonality. In view of its stability in soaps, detergents or house-hould materials, it can be moreover more widely used in perfumery than the prior known analogous odoriferous ingredients.

In the field of perfumery, compound (I) is characterized by an original odour note of black-currant type, free from sulfury tonality, reminiscent of the fruity note of black-currant buds absolute. It can be added to a great number of perfume compositions of different types such as fruity, fresh, minty, flowery, rosy, woody or chypre compositions e.g., wherein it efficiently develops its typical black-currant note.

In order to achieve such an original olfactive effect, compound (I) can advantegously be used as unique fragrant ingredient, for example in the form of solution in conventional solvents such as ethyl alcohol, diethyl phthalate, dipropylene-glycol or ethyl citrate e.g., or in admixture with the perfuming ingredients commonly used in the art, in that case in the form of a perfume base e.g. Compound (I) is appreciated in fine perfumery as well as in the preparation of perfumed products such as soaps, detergents, shampoos, cosmetics or house-hold materials, e.g.

The olfactive effects which can be achieved by making use of compound (I) greatly depend on the concentration, the nature of the fragrant coingredients or the nature of the material to which it is added. For the preparation of perfume compositions e.g., interesting effects can be achieved by using proportions as low as 0.05% of the weight of the composition. Characteristic olfactive effects are generally obtained by using compound (I) in proportions comprised between about 0.1 and 5%. Higher proportions, 20% or even more of the weight of the perfume composition can also be used, especially when particular odoriferous effects are desired.

In the field of flavours, compound (I) is characterized by its typical fruity and woody taste, reminiscent of that of black-currant. The said compound can thus be used for preparing artificial fruity flavours such as black-currant, raspberry or other red berries flavours, wherein it advantageously develops a fresh, fruity and woody flavour note, reinforcing at the same time the natural aspect of such flavour compositions.

Compound (I) can also be used for flavouring foodstuffs, beverages, pharmaceutical preparations or tobacco products. Flavouring effects such as those described hereinabove can be achieved by using the said compound in proportions comprised between about 0.01 and 10 ppm (parts per million), preferably between about 0.1 and 5 ppm of the weight of the thus flavoured material. Proportions superior to 10 ppm can also be considered, especially when particular flavouring effects are desired.

According to the process of the invention (method A) 2-ethyl-6,6-dimethyl-cyclohexanone can be first reacted with but-1-yn-3-ol, in the presence of a strong base. Suitable strong bases are mineral organic bases such as potassium hydroxide, butyl-lithium, potassium tert-butoxide or sodium or lithium amide e.g. Although this does not represent a necessary condition for achieving high yields of final product, the said reaction can be effected in the presence of inert organic solvents: in this case ethers, aliphatic or aromatic hydrocarbons or mixtures of same are preferred. The said reaction is moreover carried out at a temperature generally comprised between about 25° and 55° C., preferably of the order of 35° C.

After subsequent hydrolysis there is isolated a novel intermediate compound having the formula

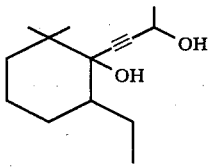

(III)

which is subsequently subjected to an acidic treatment. The said acidic treatment is effected by means of a strong mineral or organic acid, preferably in an aqueous organic medium. Suitable organic solvents are those defined in the preceeding reaction step; suitable strong acids are formic, phosphoric, sulfuric, polyphosphoric, benzenesulfonic or p-toluenesulfonic acids e.g. or even an acidic diatomaceous earth. The said acidic treatment is preferably effected at a temperature comprised between about 50° and 100° C., more generally at the boiling temperature of the reaction mixture.

According to another embodiment of the process of the invention (method A) compound (I) can also be obtained from 2-ethyl-6,6-dimethyl-cyclohexanone, by reacting the same with an organo-metallic derivative of formula

(II)

as previously defined, hydrolysis and subsequent acidic treatment of the hydrolization product. In this case, the same reaction conditions as those applied hereinabove can advantageously be used.

According to a further embodiment of the process of the invention (method B), 2-ethyl-6,6-dimethyl-cyclohex-2-en-1one can be reacted with an organo-metallic derivative of formula (II) as defined hereinabove, in the conditions of a Grignard reaction. After subsequent hydrolysis there is isolated a novel intermediate compound having the formula.

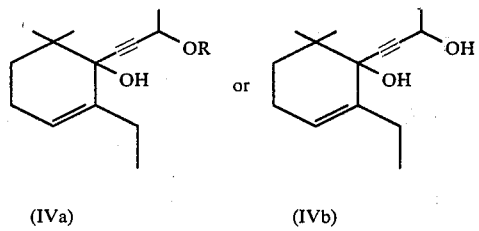

(IVa)    (IVb)

wherein R is different from Mg-halogen. The said intermediate compound is then subjected to hydrogenation, in the presence of a metal catalyst such a Raney nickel or in the presence of a partially inactivated catalyst, Lindlar catalyst e.g. There is thus obtained a further novel intermediate compound of formula

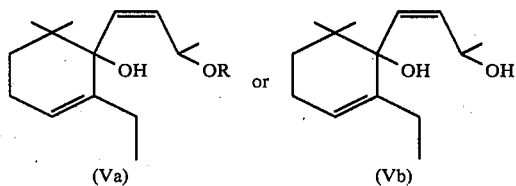

(Va)    (Vb)

wherein R is different from Mg-halogen, which is finally subjected to an acidic treatment to afford compound (I). The said acidic treatment can be effected in the same conditions as those applied for the compound of formula (III).

As obtained from the above described syntheses, compound (I) may exist in the form of a mixture of stereoisomers A and B (see hereinafter)

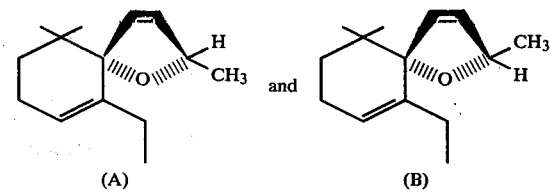

(A)    (B)

or in the form of one of the above stereoisomers. Formula (I) as defined in the invention is deemed to represent either single stereoisomers or mixtures of same. For practical and economical reasons however, compound (I) is used in accordance with the invention as directly obtained from the described process.

The invention will be illustrated in a more detailed manner by the following examples wherein the temperatures are given in degrees centigrade.

EXAMPLE 1

Preparation of
6-ethyl-2,10,10-trimethyl-1-oxa-spiro[4.5]deca-3,6-diene

Method A (i) 448 g (8 mole) of KOH and 1100 ml of di-isopropyl-ether were first introduced into a reaction vessel fitted with cooling and stirring devices. 154 g (2.2 mole) of but-1-yn-3-ol were then added to the above mixture (temperature 25°–30°; addition period:30 min), followed by 308 g (2.0 mole) of 2-ethyl-6,6-dimethyl-cyclohexanone (addition period:30 min; dropwise). The reaction mixture was then stirred at 35° for 17 hours and, after cooling, 500 ml of water were progressively added thereto. After separation of the organic phase, washing with 5% aqueous $H_2SO_4$ (200 ml), drying over $Na_2SO_4$, concentration and final distillation, there were isolated a first portion of unreacted 2-ethyl-6,6-dimethyl-cyclohexanone (46 g) and 313 g (78% yield) of 2-ethyl-6,6-dimethyl-1-hydroxyl-1-(3-hydroxy-but-1-yn-1-yl)-cyclohexane.

An analytical sample was purified by cristallization in cyclohexane, m.p. 136°.

IR: 3600, 2390, 1210, 1035, 920 $cm^{-1}$;

NMR: 1.00 (3H, t, J=7 Hz); 1.00 and 1.09 (6H, 2s); 1.48 (3H, d, J=7 Hz); 1.0–1.9 (9H, m); 1.97 (2H, broad s); 4.59 (1H, q, J=7 Hz)δ ppm;

MS: m/e=206 (7), 188 (63), 173 (76), 162 (26), 147 (100), 131 (47), 117 (54), 105 (67), 91 (79), 82 (83), 69 (58), 55 (79), 43 (88), 41 (94), 29 (62).

(ii) 100 g (0.45 mole) of the above compound in admixture with 175 g of 86% $H_3PO_4$ and 200 ml of tetrahydrofuran were heated to reflux for 20 hours. After cooling and addition of 100 ml of petrol ether (50/70), the reaction mixture was successively washed with water, then with 5% aqueous $NaHCO_3$, dried over $Na_2SO_4$, evaporated and finally subjected to fractional distillation to afford 31 g (34%) of the desired compound, b.p. 90°/2 Torr.

According to the vapour phase chromatography analysis (silicon column-UCON; 120°–180°), the thus prepared compound consists in a 1:1 mixture of stereoisomers.

IR: 1450, 1375, 1360, 1355, 1345, 1110, 1075, 1045, 1030, 1000, 970, 940, 910, 860, 830, 800, 745, 710 $cm^{-1}$;

NMR: 0.85 and 0.87 (2×1.5H, 2s); 0.93 (3H, s); 0.98 (3H, t, J=7 Hz); 1.30 (3H, d, J=6 Hz); 1.4–1.7 (2H, m); 1.7–2.2 (4H, m); 4.9 (1H, m); 5.38 and 5.49 (2×0.5H, 2m); 5.58 (1H, d×d, J$_1$=6 Hz, J$_2$=2 Hz); 5.77 and 5.84 (2×0.5H, d×d, J$_1$=6 Hz, J$_2$=1 Hz)δ ppm;

MS: m/e=150 (100), 135 (28), 121 (52), 107 (6), 91 (7), 79 (18), 67 (2), 55 (4), 43 (18), 29 (3).

2-Ethyl-6,6-dimethyl-cyclohexanone used hereinabove as starting material was prepared as follows: 600 g (3.95 mole) of 2-ethyl-6,6-dimethyl-cyclohex-2-en-1-one [prepared from n-propyl-isopropyl-ketone and acrolein; see DE-OS No. 2,547,223] were hydrogenated at room temperature and at atmospheric pressure, in the presence of 15 g of 5% palladium on charcoal. After consumption of 93 l of $H_2$ and filtration, there were isolated 601 g (99% yield) of the desired compound, b.p. 76°/12 Torr.

IR: 1705, 1450, 1380, 1365, 1130, 1035, 990 $cm^{-1}$;

MS: M$^+$=154 (20); m/e=126 (6), 82 (100), 69 (31), 56 (38), 55 (33), 41 (32), 27 (9).

Method B (i) 6.0 g (0.042 mole) of 3-(3-oxa-pent-2-yloxy)-but-1-yne were added dropwise and under nitrogen atmosphere to a mixture of 14 g (0.042 mole) of 40% ethyl-magnesium bromide in ether and 7.5 ml of anhydrous ether (addition period:30 min-temperature:20°). After having been heated to reflux for 1 hour, the reaction mixture was cooled to 20° and 3.8 g (0.025 mole) of 2-ethyl-6,6-dimethyl-cyclohex-2-ene-1-one were added thereto. The reaction mixture was stirred for 1 further hour, then cooled to 0°–5° and successively treated with 5 ml of water and 15 ml of 5% $H_2SO_4$ in water. After extraction with ether, washing, drying ($Na_2SO_4$) and evaporation of the organic layer, there were isolated 7.7 g of crude residue. Distillation thereof (150°/0.1 Torr) gave 4.4 g (59% yield) of a compound of formula

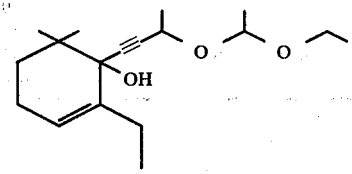

which was characterized as follows:

NMR: signals at 1.0–2.6; 3.3–4.0; 4.2–5.1; 5.3–5.6δ ppm;

MS: m/e=232 (17), 217 (11), 204 (26), 192 (39), 175 (15), 163 (26), 148 (85), 133 (96), 120 (47), 105 (80), 91 (40), 73 (59), 55 (34), 45 (100), 43 (91), 29 (40).

(ii) 2.9 g (0.01 mole) of the above compound in 20 ml of ethyl acetate were hydrogenated at room temperature, under atmospheric pressure, in the presence of 0.5 g of Lindlar catalyst ($H_2$ consumption:280 ml). After filtration and evaporation, there were isolated 2.9 g (99% yield) of a compound having the formula

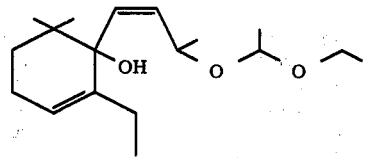

A sample thereof was purified for analysis (distillation:110°/2 Torr).

IR: 3610, 3450, 1700, 1655, 1460, 1380, 1150–1020 $cm^{-1}$;

NMR: 0.8–1.7 (20H); 1.9–2.3 (4H, m); 2.8 and 2.9 (1H, 2s); 3.2–3.9 (2H, m); 4.6–5.7 (5H, m)δ ppm;

MS: M$^+$=206 (13); m/e=194 (13), 177 (9), 163 (5), 150 (58), 135 (25), 121 (48), 107 (22), 93 (16), 79 (12), 73 (46), 55 (28), 45 (67), 43 (100), 31 (68).

(iii) 1.0 g (3.4 mmole) of the above compound in 5 ml of petrol ether (80/100) were heated to reflux for 5 hours, under nitrogen atmosphere, in the presence of 4 g of 30% $H_2SO_4$ in water. After washing of the organic layer with an aqueous solution of $NaHCO_3$, drying over $Na_2SO_4$, evaporation and distillation, there were isolated 0.6 g (86% yield) of the desired title compound.

The thus obtained compound was found identical with that prepared according to method A above.

EXAMPLE 2

A perfume base composition was prepared as follows:

| Ingredients | Parts by weight |
| --- | --- |
| IRALIA®[1] | 160 |
| Vetiveryl acetate | 100 |
| Benzyl salicylate | 100 |
| Santalol | 80 |
| Phenylethyl alcohol | 80 |
| CYCLOSIA®[1] | 80 |
| Musk ketone | 70 |
| Bergamot oil | 60 |
| Jasmin absolute, Morocco | 60 |
| Rose of may absolute | 40 |
| Synthetic civette tincture | 40 |
| Synthetic Tonkin musk tincture | 30 |
| EXALTOLIDE®[1] | 30 |
| Eugenol | 30 |
| Rose oil, Bulgary | 15 |
| Undecylenic aldehyde 10%* | 15 |
| Total | 990 |

*in diethyl phthalate
[1]origin: FIRMENICH SA, Geneva-Switzerland

The addition of 1 g of 6-ethyl-2,10,10-trimethyl-1-oxa-spiro[4.5]deca-3,6-diene to 99 g of the above base imparts thereto a fresh and fruity lifting odour, reminiscent of that of black-currant buds. The thus perfumed base composition develops a fuller and more pleasant odour than that of the original base.

EXAMPLE 3

A base perfume composition was prepared as follows:

| Ingredients | Parts by weight |
| --- | --- |
| Cetronellol | 200 |
| Benzyl benzoate | 100 |
| α-Amyl-cinnamic aldehyde | 80 |
| Hydroxy-citronellol | 80 |
| Ylang-ylang oil | 60 |
| Phenylethyl alcohol | 60 |
| HEDIONE®[1] | 40 |
| Phenoxyethyl propionate | 30 |
| α-Damascone 1%* | 20 |
| Linalol | 20 |
| Geranylacetone | 10 |
| Total | 700 |

*in diethyl phthalate
[1]origin: FIRMENICH SA, Geneva-Switzerland

The thus prepared perfume base is characterized by a generic flowery odour.

The addition of 300 g of 6-ethyl-2,10,10-trimethyl-1-oxa-spiro[4.5]-deca-3,6-diene to 700 g of the above base imparts thereto a typical fruity note of black-currant type. The thus obtained "black-currant" perfume composition may be harmoniously combined with many other perfume compositions, of various types.

EXAMPLE 4

100 mg of 6-ethyl-2,10,10-trimethyl-1-oxa-spiro[4.5]deca-3,6-diene were incorporated into 100 g of commercial soap having a neutral odour. The thus perfumed paste was then used for the manufacture of toilet soap bars which were finally subjected to olfactive evaluation. It was noted that the perfumed soap bars developed a pleasant fruity odour of black-currant type.

EXAMPLE 5

A black-currant syrup—prepared from 1 part of concentrated commercial syrup and 9 parts of water—was flavoured with 6-ethyl-2,10,10-trimethyl-1-oxa-spiro[4.5]deca-3,6-diene, at a rate of 5 ppm.

After comparison with an unflavoured (control) diluted syrup, it was noted that the flavoured syrup possessed a fuller, rounder and more natural taste together with a typical fruity and woody note.

What I claim is:

1. Compound of formula

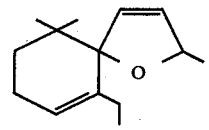

(I)

* * * * *